US00PP37821P2

(12) United States Plant Patent
Hansen

(10) Patent No.: US PP37,821 P2
(45) Date of Patent: Oct. 27, 2026

(54) ***DICENTRA* PLANT NAMED 'Passion Hearts'**

(50) Latin Name: ***Dicentra* hybrid**
Varietal Denomination: Passion Hearts

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 1 day.

(21) Appl. No.: 18/831,860

(22) Filed: Oct. 14, 2025

(51) Int. Cl.
*A01H 5/02* (2018.01)
*A01H 6/64* (2018.01)

(52) U.S. Cl.
USPC ..... Plt./426

(58) Field of Classification Search
USPC ..... Plt./426
See application file for complete search history.

(56) References Cited

U.S. PATENT DOCUMENTS

PP32,380 P2 * 10/2020 Hansen ..... A01H 6/64
Plt./360

* cited by examiner

*Primary Examiner* — Susan Mccormick Ewoldt
*Assistant Examiner* — Zachariah Allan Kay

(57) ABSTRACT

A new and unique Fern-leaf Bleeding Heart, *Dicentra* plant named 'Passion Hearts' characterized by medium-size habit and deeply-lobed, triternate, bluish-green foliage. The large pendulous flowers heart-shaped, rosy-pink with purplish-red tips on large heavily-branched peduncles with numerous flowers beginning late April and continuing for 26 weeks. The new plant has an excellent growth rate.

2 Drawing Sheets

Botanical classification: *Dicentra* hybrid.
Variety denomination: 'Passion Hearts'.

STATEMENT REGARDING PRIOR DISCLOSURES UNDER 37 CFR 1.77(b)(6)

The Applicant asserts that no publications or advertisements relating to sales, offers for sale, or public distribution occurred more than one year prior to the effective filing date of this application. The first offer for sale was by Walters Gardens, Inc. on Oct. 15, 2024, to North Coast Perennials. Walters Gardens, Inc. obtained the new plant and all information about the new plant directly from the inventor. Any information or disclosure about the claimed plant less than one year prior to the effective filing date of this application would have been obtained directly or indirectly from the Inventor and would be a 35 U.S.C. 102(b) exception.

BACKGROUND OF THE INVENTION

The present invention relates to the new and distinct *Dicentra spectabilis* 'Passion Hearts' hereinafter referred to by the cultivar name 'Passion Hearts' and the new plant. 'Passion Hearts' is the result of a cross of the proprietary unnamed hybrid known only by the breeder code 15-3-x (not patented) as the female or seed parent x the proprietary unnamed hybrid known only by the breeder code 15-1-1 (not patented) as the male or pollen parent on August 23, 2017, at a wholesale perennial nursery in Zeeland, Michigan, USA. Through trials at a wholesale perennial nursery the plant was referred to by the code 17-10-1. The new plant has been successfully asexually propagated initially by division in 2019 followed by shoot tip tissue culture at the same nursery in Zeeland, Michigan. Both these asexual propagation systems have been found to produce stable and identical plants that maintain all the unique characteristics of the original plant in successive generations.

BRIEF DESCRIPTION OF THE INVENTION

The new plant can be most closely compared with: 'Amore Pink' U.S. Plant Patent No. 25,601, 'Amore Rose' U.S. Plant Pat. No. 25,623, 'Candy Hearts' U.S. Plant Pat. No. 14,692, 'Luxuriant' U.S. Plant Pat. No. 3,324, and 'Pink Diamonds' U.S. Plant Pat. No. 32,380.

'Amore Pink' has fewer flowers per peduncle over a shorter season, the flowers are smaller and more pale purple. 'Amore Rose' has fewer flowers per peduncle, flowers for a shorter season, and smaller flowers of darker purplish-red. 'Candy Hearts' has shorter peduncles with fewer and smaller flowers, and the habit is smaller. 'Luxuriant' has a smaller habit, foliage that is less glaucous and more light green, and the flowers are smaller and lighter pink. 'Pink Diamonds' has smaller flowers that are lighter pink.

The female parent is less floriferous with taller panicles and more open habit. The male parent has more green and less bluish-green foliage and has a darker red flower on shorter panicles. Neither parent was as long lived in the landscape.

The new plant, 'Passion Hearts', is unique from all Fern-leaf Bleeding Hearts known to the inventor by the following combined traits:

1. Medium-sized habit with deeply-lobed, triternate, bluish-green foliage;
2. Large pendulous flowers are heart-shaped rosy-pink and purplish-red petals;
3. Large heavily-branched racemes have numerous flower beginning in late April and continuing for 26 weeks.

BRIEF DESCRIPTION OF THE DRAWINGS

The color drawings illustrate the overall characteristics of the new plant and demonstrate the overall appearance of the new plant including the unique traits as a three-year-old plant growing in a full-sun trial garden in Zeeland, Michigan with supplemental water and fertilizer as needed. The colors are as true as reasonably possible given the technology available. The colors are as accurate as reasonably possible with color reproductions. Ambient light, spectrum, temperature, source, duration and direction may cause minor variation in appearance.

DETAILED DESCRIPTION OF THE INVENTION

Figure 1:
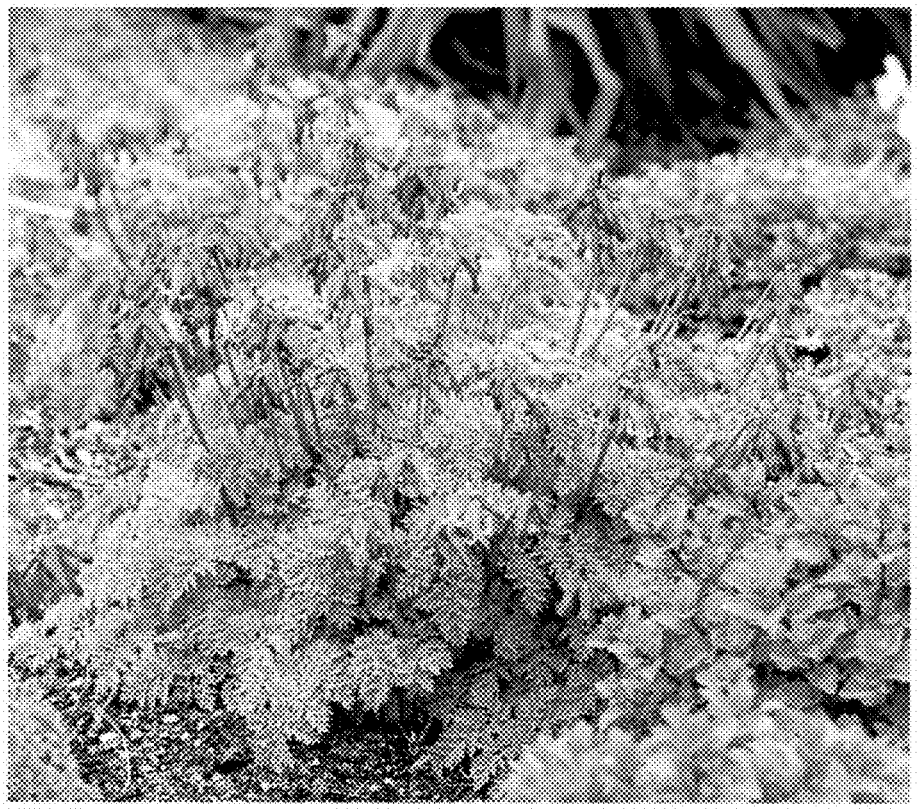
FIG. 1 shows the new plant grown in a full-sun trial garden in early flowering.
Figure 2:
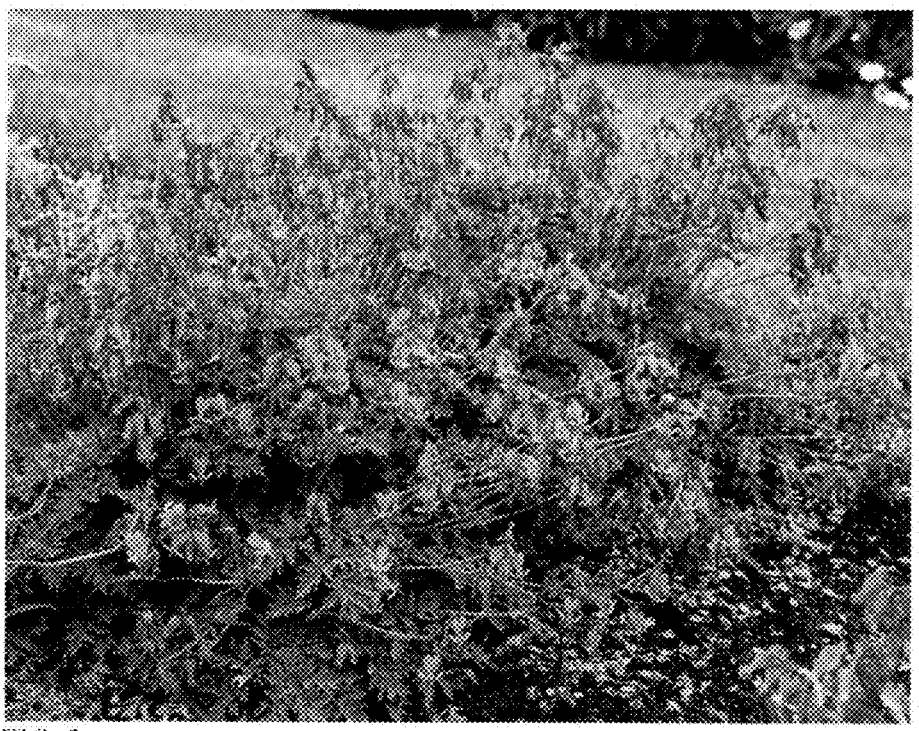
FIG. 2 shows the new plant grown in a full-sun trial garden in mid-season flowering.
Figure 3:
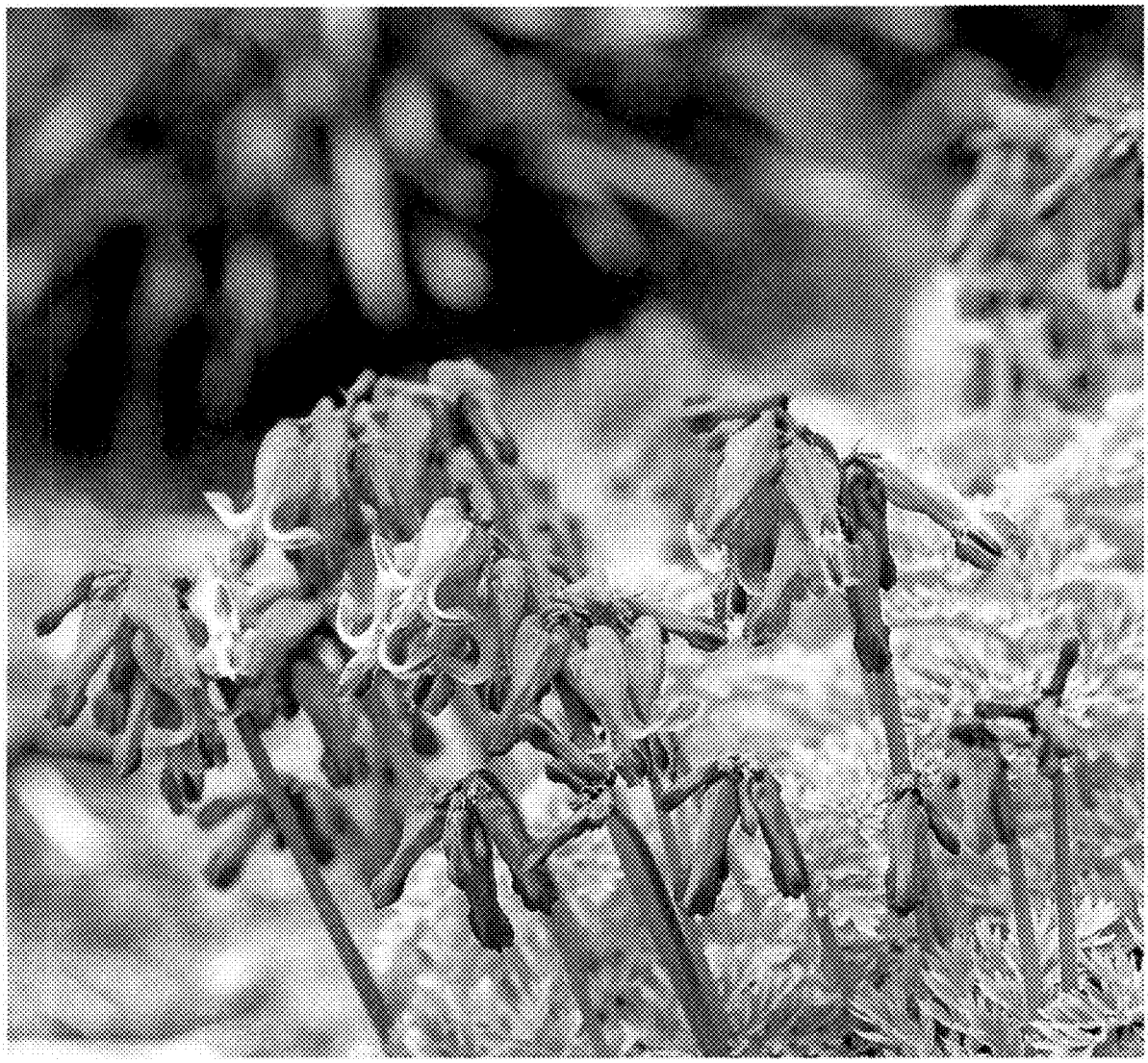
FIG. 3 shows a close-up of the flowers and buds in early flowering.

The following detailed description is based on a three-year-old plant growing in a full-sun trial garden in Zeeland, MI, USA. Except for ordinary dictionary color usage, color references are according to The Royal Horticultural Society Colour Chart, 2015 edition.

Parentage: Female or seed parent is 15-3-x; male or pollen parent is 15-1-1;

Asexual propagation: Plant tissue culture, time to finish from a 65 mm plug to a 3.8-liter container about 5 weeks following vernalization;

Roots: Finely branching; color nearest RHS 161D depending on soil substrate and nutrition;

Plant habit: Herbaceous, winter-hardy perennial; forming compact rounded mound with about 18 stems;

Size: Foliage grows to 28 cm tall and 45 cm wide; flowering to 40 cm tall and 65 cm wide; foliage continues growing in the heat of summer;

Stem: Cylindrical; glabrous; to 1 cm long and 8 mm diameter at base; covered with petioles;

Vigor: Excellent; growing best in well-drained soil in partly shade conditions;

Leaf: Triternate to irregularly divided; deeply lobed; deltoid in outline; to 10.5 cm long and 10 cm wide; glabrous and glaucous both adaxial and abaxial;

Primary leaflets: To about 7.5 cm long and 6 cm wide;

Secondary leaflets: 2 to 5-lobed; overall outline ovate; center leaflet to about 6.5 cm long and 6 cm wide; side leaflet to about 7 cm long and 6 cm wide;

Lobes: Oblanceolate to lanceolate; apex acute, base fused with other lobes in the proximal one-quarter; margin entire; to about 2 cm long and 1.5 cm wide;

Leaf color: Emerging and developing adaxial nearest RHS 138A, emerging and developing abaxial nearest blend of RHS 138B and RHS 138A, without anthocyanins; mature adaxial between RHS 139B and RHS 139A, mature abaxial RHS 139B and RHS 139A;

Venation: Pinnate; glabrous adaxial and abaxial; costate abaxial; slightly indented abaxial;

Vein color: Adaxial RHS 139B and RHS 139A, abaxial nearest RHS 146D in proximal midrib and between RHS 146D and RHS 139D in distal midrib and secondary veins;

Petiole: Concavo-convex; glabrous; flexible; to 15.5 cm long, 5 mm across above partially clasping base, and about 1 cm above base about 3 mm across;

Petiole color: Distally nearest RHS 146B; proximally nearest RHS 147C and moderately micro-maculate with nearest and RHS 183A;

Rachis: Cylindrical with adaxial grooved channel; glabrous; glaucous; flexible; to 4.9 cm long and 2 mm diameter;

Petiolule: Concavo-convex; glabrous; glaucous; flexible; to 3 cm long and 2 mm diameter;

Rachis and petiolule color: Nearest RHS N138C;

Inflorescence: Raceme; about 50 per plant flowering at one time; aspect upwardly and slightly outwardly; flowering in the distal 13 cm;

Number of flowers: About 80 to 115 per raceme;

Peduncle: Cylindrical; with longitudinal ridges; glabrous; slightly glaucous; to 42 cm long and 4 mm diameter; aspect mostly upwardly;

Peduncle color: Proximally nearest RHS N148B, distally between RHS 183D and RHS 59B;

Branches: About 7 per peduncle; cylindrical; glabrous; slightly glaucous; at approximately a 30 degree angle above horizontal; to about 8.5 cm long and 2 mm diameter at main stem; color nearest RHS 146C proximally and ventrally, dorsally and distally where exposed to high light maculate to solid nearest RHS N186B;

Pedicel: Cylindrical; glabrous; slightly glaucous; to about 4 mm long and about 0.7 mm diameter;

Pedicel color: Nearest RHS N186B where exposed to high light, nearest RHS N148B in shadows;

Foliar bract: At peduncle branches; linear; glabrous; narrowly acute margin; truncate base; entire margin; to about 6 mm long and 1 mm across at base; color between RHS 183D and RHS 59B;

Flower bud: One day prior to opening inverted vase-shaped, narrowest in middle; base cordate; apex acute; to about 25 mm long, 13 mm wide and 10 mm thick at the base, about 5 mm diameter in middle and near apex 3 mm across, with wings extending to about 9 mm across;

Flower bud aspect: Mostly drooping;

Flower season: Beginning late April and continuing for about 26 weeks;

Flower lastingness: Individual flower last about one week; each raceme lasts about 3 weeks;

Bud color: One day prior to anthesis proximally between RHS 67C and RHS 67D with veins and midrib nearest RHS 67B, distal petal arms and wings between RHS 70A and RHS 72B;

Bud color: Three days prior to anthesis proximally nearest RHS 59C, distally nearest RHS 71A, and wings nearest RHS 59A;

Flower: Zygomorphic; proximally cordate; laterally slightly applanate; with two sets of petals; about 26 mm long, 13 mm wide near base, 9 mm thick, 4 mm wide at constriction, 19 mm wide at reflexed outer petal apices, 4 mm wide near inner petal apex, protruding wings to 9 mm wide;

Flower aspect: Drooping;

Corolla: Outer petals opposite, inflated proximally, concavo-convex and reflexed distally, glabrous, fleshy and stiff; apex acute, basal 3 mm connate with opposite petal; margin entire; to 24 mm long extended and 19 mm long in reflexed state, 9 mm wide near base, and 4 mm wide from constriction near apex; inner petals opposite, at right angle to outer set; spatulate with distal portion fleshy and cupped, apex acute and fused in distal 1 mm; to about 23 mm long and 3 mm across in constricted portion, 2 mm wide and folded in basal 8 mm, with keeled, central, protruding wing in distal 8 mm extending about 3 mm;

Petal color: When first open-outer petal adaxial base nearest RHS 69C, middle nearest RHS 69C moderately maculate with nearest RHS 70B, and distally nearest RHS 70B; when first open-outer petal abaxial base between RHS 64C and RHS 64B with veins nearest RHS 64B, abaxial apex nearest RHS 70A, and wing nearest RHS 71A; when mature-outer petal adaxial base nearest RHS 69D, middle nearest RHS 69D moderately maculate with nearest RHS 70B, and distally nearest RHS 70A; when mature-outer petal abaxial base nearest RHS 64C with veins nearest RHS 64B, abaxial apex nearest RHS N75A, and middle portion nearest RHS 75B; with base and distal veins nearest RHS N155D; inner petal adaxial proximal folded portion nearest RHS N155B on margins and nearest RHS 70B in center, apex nearest RHS 72B, central portion at base of wing nearest RHS N186B; inner petal abaxial proximal 8 mm portion margins nearest RHS NN155C and center nearest RHS 72B, center 6 mm margins between RHS75B and RHS 70D and center nearest RHS 72B, wing and margin between RHS 64A and RHS 72A and where wing attaches to petal nearest RHS 73D;

Sepals: Two; at right angles to outer petals; ovate; acute apex; truncate base; micro-serrulate margin; glabrous; to about 5 mm long and 3 mm wide near base;

Sepal color: Adaxial and abaxial between RHS 59A and RHS N77B;

Gynoecium: Single; 20 mm long; erect, straight;

Style: About 9 mm long and 1 mm diameter at ovary, tapering toward stigma; persists with mature fruit; color nearest RHS 177D;

Stigma: With two apices about 1.5 mm long protruding from a base about 1.5 mm across and 1 mm thick; color nearest RHS 157D;

Ovary: Superior; oblong fusiform; apex narrowly acute, tapering toward style; base truncate; 12 mm long and 3 mm diameter near middle; color between RHS 176B and RHS 197A;

Androecium: Six; anthers and distal one-half of filaments connate into two groups;

Filaments: Six; petaloid; arcuate 180 degrees in the basal 5 mm, connate in a 3 mm long section about 3 mm from anther, free in distal 3 mm; petaloid bases separate; in two groups at right angle to inner petals; two lateral and one central petaloid in each group; two lateral filaments to about 2 mm wide near base and about 21 mm long straightened, central filament to about 2 mm wide near base and about 22 mm long stretched, both lateral and central filament narrowed to about 0.2 mm diameter in distal 6 mm; color nearest RHS 69C proximally and distally nearest RHS NN155D;

Anthers: Closely arranged just below stigma; longitudinal ellipsoid; about 2.5 mm long and 0.7 mm across; color nearest RHS 10A;

Pollen: Abundant; color nearest RHS 13B;

Fragrance: Faint, lightly sweet;

Fruit and seed have not yet been observed under the present growing conditions.

Pest and disease tolerance: 'Passion Hearts' has not shown susceptibility to insects of the sub-families Aphidoidea and Aleyrodoidea or fungi of unknown scientific names that are frequent pests and diseases of other cultivars in the genus *Dicentra.*

I claim:

1. A new and distinct cultivar of Fern-leaf Bleeding Heart, *Dicentra* plant named 'Passion Hearts' as herein described and illustrated.

* * * * *